United States Patent [19]

Endicott et al.

[11] Patent Number: 4,788,060

[45] Date of Patent: Nov. 29, 1988

[54] MULTIPLE ELECTROLYTE DOUCHE AND WIPE COMPOSITION

[75] Inventors: Clarence J. Endicott, Libertyville; Donald E. Hartung, Arlington Heights, both of Ill.

[73] Assignee: Abbott Laboratories, Abbott Park, Ill.

[21] Appl. No.: 923,788

[22] Filed: Oct. 27, 1986

[51] Int. Cl.[4] .......................... A61K 9/70; A61M 5/18; B65D 83/10; A01N 59/00

[52] U.S. Cl. ................... 424/443; 128/200.22; 206/363; 206/438; 206/570; 424/127; 424/153; 424/430; 604/36; 604/37; 604/55; 514/557; 514/967

[58] Field of Search ............... 604/217, 55, 36-38, 604/215, 216, 217; 206/438, 557, 363, 812, 570, 364, 823, 828; 424/967, 430, 443; 128/200.22; 514/557, 967; 427/127, 153

[56] References Cited

U.S. PATENT DOCUMENTS

| | | | |
|---|---|---|---|
| 2,556,567 | 6/1951 | Wright et al. | 424/145 |
| 2,649,398 | 8/1953 | Wright et al. | 424/145 |
| 2,999,265 | 9/1961 | Duane et al. | 206/812 X |
| 3,150,049 | 9/1964 | Emory | 206/812 X |
| 3,219,525 | 11/1965 | Berkow et al. | 424/45 |
| 3,786,615 | 1/1974 | Bauer | 206/812 X |
| 4,300,555 | 11/1981 | Kopito | 604/212 X |
| 4,537,807 | 8/1985 | Chan et al. | 206/812 X |
| 4,722,936 | 2/1988 | Jacob | 514/474 |

*Primary Examiner*—Thurman K. Page
*Attorney, Agent, or Firm*—D. O. Nickey; M. L. Katz; M. M. O'Brien

[57] ABSTRACT

A disposable feminine hygiene kit and system that includes a douche composition for internal cleansing of the vagina, and a wipe solution for external cleansing of the vulva. The douche formulation may be a ready-to-use liquid solution, or a concentrate. It comprises inorganic salts, as well as a buffering agent for pH adjustment. The concentrate does not require a preservative. The ready-to-use liquid solution incorporates the ingredients of the concentrate, and also includes a preservative. The compositions of both the liquid and the concentrate comprise a multiple electrolyte solution, pH-adjusted and isotonic (after dilution of the concentrate), resulting in optimal vaginal compatibility. The douche composition is used in combination with a preserved anti-bacterial wipe solution for use upon the external vulva. The wiping solution is preferably incorporated into a towelette application.

36 Claims, No Drawings

MULTIPLE ELECTROLYTE DOUCHE AND WIPE COMPOSITION

FIELD OF THE INVENTION

This invention relates to a disposable feminine hygiene system. More particularly, the present invention relates to a disposable douche solution comprising a multiple electrolyte solution, pH-adjusted and isotonic, employing only natural ingredients, that cleanses the vagina internally with optimal tissue compatibility, safety, and efficacy. It also relates to an anti-bacterial external vulval wipe that cleanses, deodorizes, and relieves itching of the external female genitalia. The douche composition may be a ready-to-use liquid solution, or a concentrate which requires dilution with water before use.

BACKGROUND OF THE INVENTION

It is desirable that a product for general douching purposes have an effective cleansing action on the vaginal surfaces, that it be mildly astringent, and that it have an acidity approximating that of the normal vagina, i.e., a pH between 3.0 and 6.0, and preferably between 4.0 to 5.0. The douche must not interfere with the natural reaction of the vaginal tract or disturb the development of a normal bacterial flora which is generally cosidered essential to the maintenance of a healthy condition.

Hence, it is important that the douche be capable of establishing and maintaining the desired acidity. Further, it is important that the douche solution be free from components which would destroy certain bacilli which are normally and desirably present in the vagina. It is also desirable in the case of a solution that is to come in contact with a permeable membrane such as that of the vaginal surface, that the solution be approximately isotonic or perhaps somewhat hypertonic so that the solution has a balanced electrolyte concentration equivalent to or somewhat greater than that of the normal body electrolyte composition. Furthermore, the ingredients should be non-toxic and free from irritating and other deleterious properties, and be chemically and physically stable so that the composition may be stored over a relatively long period of time without deteriorating.

It is extremely important that the proper types, combinations, and concentrations of multiple electrolytes be used in this invention, since it is well established in basic tissue culture studies that living cells survive better and are more healthy in an isotonic, multiple electrolyte composition than in simple isotonic saline (sodium chloride).

It is equally desirable to have an effective solution for the external cleansing of the vulva. The external cleansing solution (i.e. the wipe) should contain an anti-bacterial, anti-inflammatory, and anti-allergic agent for effectively cleansing and relieving irritation of the vagina. The wipe solution should also have a pH similar to that of the vagina, approximately 3.5 to 4.5. As in the case of douche solutions, the external wipe should also be non-toxic and free from irritants, and be chemically and physically stable so that the material may be stored without deteriorating. It is further desirable to use the wipe solution in conjunction with the douche solution in order to cleanse the entire vaginal area.

The relevant prior art includes U.S. Pat. No. 3,219,525, which discloses the use of combinations of lactic, citric or acetic acid with sodium bicarbonate, sodium lactate, sodium citrate or sodium acetate to obtain a suitable pH for a douche product employing one or more quaternary detergents.

U.S. Pat. No. 2,649,398 discloses the use of citric acid in a douche, and also discloses the desirability of having an isotonic concentration of sodium chloride in a detergent solution.

U.S. Pat. No. 2,556,567, also discloses a douche solution with an isotonic concentration of sodium chloride in a detergent solution.

U.S. Pat. No. 3,346,450 discloses the desirability of having a douche with a pH of 3.5 to 5.0.

U.S. Pat. No. 4,568,540 discloses the use of sodium gluconate as a buffering agent to maintain a pH of 3.5 to 6.0 in an oral hygiene composition.

U.S. Pat. No. 4,581,226 discloses the use of diluted sterilized seawater for treating sensitive animal tissue. The seawater is diluted to make it isotonic with the tissue to be treated. This patent also mentions use of this seawater solution as a vaginal douche, but the solution disclosed therein is not a balanced electrolyte medium; i.e. it has a different electrolyte composition from human tissue.

U.S. Pat. No. 4,556,557, discloses the use of sorbic acid as a preservative in a product used for treating the nasal mucosa.

An article entitled "Methods of Use of Waters with High Sodium Chloride Content," Presse Therm. Clim., 112/1, 15–16 (1975) (in French) discloses the use of a mineral water douche. In addition to NaCl, the solution also contains potassium chloride and magnesium chloride.

Other relevant articles include "Salt Therapy," Therapiewoche, 30/40, 6564–6571 (1980) (in German) which discloses the use of brine douches; Therapiewoche, 31/29 4726–4729 (1981) (in German) which discloses the use of natural water for douching; and "Contact Dermatitis," Cutis, 8, 341–342 (1982) discloses that sorbic acid is a suitable preservative for use in products for treatment of the oral mucosa.

Normosol solution (trademark of Abbott Laboratories), is a product use intravenously in hospitals as an irrigation solution and electrolyte replenisher. Normosol formulas are sterile, non-pyrogenic solutions of balanced electrolytes in water for injection. The solutions contain no bacteriostat, anti-microbial agent or added buffer (except for pH adjustment).

The present invention incorporates Normosol solution, but uses citric acid to adjust pH instead of hydrochloric acid. Normosol solution has a pH of 6.4, whereas the final pH of the present invention ranges from 3.5 to about 4.5. The normal vagina has a pH range of 3.0 to 6.0. Usually, the pH of the vagina falls between 4.0 and 5.0. The pH of Normosol solution is well above the pH of the normal vagina, and hence it would be ineffective as a vaginal cleansing agent. Thus, the substitution of citric acid in place of hydrochloric acid creates a novel composition which is effective for douching. It should also be noted that Normosol solution, being sterile, does not have sorbic acid as a preservative.

There are several topical anti-infective, antiseptic solutions used to soothe and heal mild skin abrasions and irritations. One such product is Lady Protex, from National Sanitary Laboratories, comprising: benzalkonium chloride, octoxynol 9, water, propylene glycol, menthol, propyl paraben, citric acid, and fragrance. Another product is Bidette from Young Drug Products, comprising: water, ethyl alcohol, polysorbate 20, benzalkonium chloride, menthol, sodium bicarbonate, and fragrance.

Although the prior art thus exhibits a variety of relatively safe and reliable douching and topical anti-infective formulations, there are problems with the compositions and effectiveness of these existing formulations.

First, the douche products disclosed, with the exception of seawaterm, contain detergents. The more common douching detergents include dioctyl sodium sulfosuccinate, nonoxynol, octoxynol, and sodium lauryl sulfate. These detergents are among the few ingredients endorsed by the FDA and the OTC panel as acceptable for use in non-prescription douche products. Thus, douche solution alternatives are limited. The seawater solution alone (disclosed in U.S. Pat. No. 4,581,226), without the addition of various amino acids and substrates, is not a balanced electrolyte solution as is the invention herein.

Second, the detergents used in the existing douche products may also cause vaginal irritation due to differences between the douche solutions and the natural vaginal physiological fluids.

Third, although the prior art discloses the desirability of douche solutions with suitable pH's and isotonic concentrations, no solution to date achieves that result with balanced electrolytes for optimal tissue safety and also uses nothing but natural ingredients in an electrolyte solution.

Fourth, the products that are applied topically differ in their composition and mode of application. The invention herein is applied to the external vulva by an anti-bacterial saturated towelette.

Fifth, the existing douche products require precise mixing before use and are limited to internal cleansing of the vagina. There is no prior art that discloses a disposable hygiene system that is suitable for both internal vaginal and external vulval cleansing.

BRIEF SUMMARY OF THE INVENTION

The objectives, features, and advantages of the present invention are achieved by a disposable feminine hygiene kit and system that includes a douche composition for internal cleansing of the vagina and a wipe solution for external cleansing of the vulva.

The douche formulation may be a balanced electrolyte liquid solution or a concentrate. The douche concentrate comprises inorganic salts as well as a buffering agent for pH adjustment. The concentrate formulation has a high enough salt concentration to be self-preserving, and therefore does not require a preservative. The douche liquid solution incorporates the ingredients of the concentrate, and also includes a natural preservative such as sorbic acid. The compositions of both the liquid and the concentrate comprise a multiple-electrolyte solution, pH-adjusted and isotonic (after dilution of the concentrate), resulting in optimal vaginal compatibility.

The douche composition is combined with an anti-bacterial wipe solution for use upon the external vulva. The wipe solution comprises a non-greasy oil ingredient, one or more non-ionic surfactants, a solvent, a preservative, an anti-inflammatory and anti-allergic agent, a buffering agent, and purified water. The wiping solution is preferably incorporated into a towelette applicator.

DETAILED DESCRIPTION OF THE INVENTION

The present invention contemplates a disposable douche solution and concentrate in the form of a balanced electrolyte solution, pH-adjusted, and istonic (after dilution of the eoncentrate), as well as an external anti-bacterial wipe designed to be used used therewith. The douche formulation (solution or concentrate) comprises an effective concentration of inorganic salts that mimic the electrolyte balance of normal healthy tissue and include the following: sodium acetate, sodium chloride, magnesium chloride, potassium chloride, and sodium gluconate. Citric acid is used as a buffering agent to adjust the pH, and sorbic acid acts as a preservative in the douche solution. The douche concentrate formulation, on the other hand, contains no sorbic acid, since the salt concentrations are high enough to be self-preserving, and after a batch of concentrate is diluted it is expected to be consumed promptly.

The inorganic salts are the same type and concentration of electrolytes present in healthy vaginal tissue. Sodium chloride, potassium chloride, magnesium chloride and sodium acetate are all essential electrolytes in the solution that insure optimal vaginal tissue compatibility. These electrolytes in proper concentration cause the solution to be isotonic.

Sorbic acid in the douche solution acts as a preservative. It is omitted from the douche concentrate formulation to provide a preservative-free system.

Citric acid is added to lower the pH to the range of 3.5 to 4.5. The use of citric acid is preferable since it results in a more compatible pH with that of the vaginal fluid. Lactic acid is an alternative ingredient which can be used to adjust the pH of the solution to 4.0.

The preferred procedure for manufacturing the disposable douche formulation is as follows. Sorbic acid, used as a preservative, is added to distilled or deionized water. It is used only in the liquid formulation, however, and not in the concentrate formulation. Heat may be applied to speed the dissolution of the sorbic acid. The inorganic salts: sodium chloride, potassium chloride, magnesium chloride, sodium acetate, and sodium gluconate; are then added individually to the water. Each salt is allowed to dissolve completely before the next is added. Citric acid is then added to lower the pH range to 3.5 to 4.5. The amount and percent concentration of each ingredient may be seen in the tables below.

| Douche Concentrate (pH = 3.5 to 4.5) | | |
|---|---|---|
| Ingredient | % Concentration by Weight | Scale/Liter |
| Sodium Chloride | 16.56 + 0.516 − 0.512 | 165.6 cc. |
| Sodium Gluconate | 15.80 + 0.492 − 0.512 | 158.0 cc. |
| Sodium Acetate | 7.0 + 0.212 − 0.232 | 70.0 cc. |
| Potassium Chloride | 1.17 + 0.032 − 0.042 | 11.7 cc. |
| Magnesium Chloride, Hexahydrate | 0.93 + 0.025 − 0.035 | 9.3 cc. |
| Citric Acid | 6.0 + 0.25 − 0.50 | 60.0 cc. |
| Water, Purified | q.s. | to 1 liter |

When diluted to the proper volume (1 quart) the actual use concentration of the formula is:

| | |
|---|---|
| 0.526% | Sodium Chloride |
| 0.502% | Sodium Gluconate |
| 0.222% | Sodium Acetate |
| 0.037% | Potassium Chloride |
| 0.030% | Magnesium Chloride |
| 0.19% | Citric Acid |

The balance is water.

| Douche Solution (liquid) (pH = 3.5 to 4.5) | | |
|---|---|---|
| Ingredient | % Concentration by Weight | Scale/Liter |
| Sodium Chloride | 0.526 + 0.516 − 0.536 | 5.26 g. |
| Potassium Chloride | 0.037 + 0.032 − 0.042 | 0.37 g. |
| Magnesium Chloride Hexahydrate | 0.03 + 0.025 − 0.035 | 0.30 g. |
| Sodium Acetate | 0.222 + 0.212 − 0.232 | 2.22 g. |
| Sodium Gluconate | 0.502 + 0.492 − 0.512 | 5.02 g. |
| Citric Acid | 0.35 + 0.25 − 0.50 | 3.50 g. |
| Sorbic Acid | 0.1 + 0.09 − 0.11 | 1.00 g. |

The present invention also comprises an anti-bacterial wipe solution. The wipe solution is used for external vulval cleansing in combination with the above-described multiple-electrolyte internal douche solution. The wipe solution comprises a non-greasy oil ingredient, non-ionic surfactants, a preservative, an anti-inflammatory and anti-allergic agent, an acid, and purified water. An organic solvent preferably also is included.

The preferred non-greasy oil is caprylic/capric triglyceride. This ingredient makes the tissue smooth. Since caprylic/capric triglyceride is not soluble in water, one or more non-ionic surfactants, such as sorbitan stearate and polysorbate (United States Adopted Name for a polyoxyethylene fatty acid ester. A group of non-ionic surfactants obtained by esterification of sorbitol with a fatty acid.) 60 in combination, are employed to emulsify the oil and thereby produce a homogeneous composition. In order for the surfactant to emulsify the oil, the ratio of sorbitan stearate to polysorbate 60 must be 60% to 40%, respectively. This ratio improves the physical stability of the solution. If an organic solvent is also included in the wipe solution, the preferred choice is propylene glycol which is miscible with water and will dissolve many essential oils. The preservative ingredient herein is Germaben II E, a prepared mixture of methyl paraben, propyl paraben, imidazolidinyl urea, and propylene glycol. The use of this combination of preservatives improves the microbiological profile. The anti-inflammatory and anti-allergic agent is hydrocortisone acetate. The acid is citric acid which gives the solution an adjusted pH of 3.5 to 4.5, depending upon the concentration. Finally, purified water is added to the solution to bring it to its final proportions.

The procedure for formulating the wipe solution is as follows. Distilled or deionized water, equal to 75% of the final batch weight, is added to a suitably sized tank. The water is heated to 70°–75° C. As the water is being heated, propylene glycol is added.

In a separate tank, the oil phase ingredients—caprylic/capric triglyceride, polysorbate 60, and sorbitan stearate—are combined and heated to 70°–75° C.

When both the water phase and the oil phase are within the desired temperature range, the oil phase is added to the water phase while the tank is agitated. After fifteen minutes, agitation can be reduced and forced cooling started.

When the batch temperature is below 50° C., citric acid and the preservatives can be added, followed by hydrocortisone acetate.

When the batch has reached 30° C., cooling can be stopped. The pH is then checked and additional citric acid added, if necessary, to obtain a pH of 3.5 to 4.5.

Sufficient distilled water or deionized water is then added to bring the batch to its final weight.

The amount and concentration of each ingredient used in the wipe solution may be seen in the table below.

| | % Concentration | | |
|---|---|---|---|
| Ingredient | Range | Preferred | Scale/Kg |
| Caprylic/capric triglyceride (Neobee M-5) | 5 to 20% | 10 | 100 g. |
| Sorbitan Stearate (60%) (Arlacel 60) | 2 to 4% | 3.0 | 30 g. |
| Polysorbate 60 (40%) (Tween 60) | 1 to 3% | 2.0 | 30 g. |
| Propylene glycol | 5 to 15% | 5.0 | 50 g. |
| Gerbaben II E: | | 1.0 | 10 g. |
| (a) methyl paraben (10%) | | | |
| (b) propyl paraben (10%) | | | |
| (c) Imidazolidinyl urea (20%) | | | |
| (d) propylene glycol (60%) | | | |
| Hydrocortisone acetate | 0.5 | | 5 g. |
| Citric acid | 0.02 | | 0.2 g. |
| Water, purified | q.s. | | to 1 L. |

The wipe solution is preferably impregnated in a suitable towelette means, i.e. a non woven polyester material of approximately 17 mils.

It will now be appreciated that the present invention provides a significant improvement in feminine hygiene preparations, in that it provides a kit and system for both internal and external care of the genitalia, and also in that the internal douche and external wipe formulations of this kit and system are both superior in various respects to any prior art formulations for such purposes.

The foregoing description is for purposes of illustration, rather than limitation of the scope of protection accorded this invention. The latter is to be measured by the following claims, which should be interpreted as broadly as the invention permits.

What is claimed is:

1. A kit containing both (a) an internal vaginal douche in the form of either a ready-to-use solution or a concentrate to be diluted, and (b) an external vulval wipe product wherein said douche comprises (1) a solution of inorganic salts that mimic the electrolyte balance of normal tissue selected from the group comprising sodium acetate, sodium chloride, magnesium chloride, potassium chloride and sodium gluconate; (2) a buffering agent, and optionally; (3) a preservative, and wherein said external vulval wipe product is a towelette impregnated with a solution which comprises (a) caprylic/capric triglyceride; (b) at least one non-ionic surfactant; (c) an anti-inflammatory agent; and (d) citric acid.

2. The kit of claim 1 wherein said vaginal douche comprises a ready-to-use solution.

3. A system for internal and external feminine hygiene comprising an internal vaginal douche formulation and an external vulval wipe product, wherein said douche formulation comprises (1) a solution of inorganic salts the mimic the electrolyte balance of normal tissue selected from the group comprising sodium acetate, sodium chloride, magnesium chloride, potassium chloride and sodium glucontae; (2) a buffering agent, and optionally; (3) a preservative, and wherein said external vulval wipe product is a towelette impregnated with a solution which comprises (a) caprylic/capric triglyceride; (b) at least one non-ionic surfactant; (c) and anti-inflammatory agent; and (d) citric acid.

4. The system of claim 3 wherein said electrolyte solution comprises an aqueous solution of sodium chloride, potassium chloride, magnesium chloride hexahydrate, sodium acetate, and sodium gluconate.

5. The system of claim 3 wherein said douche formulation is in the form of a ready-to-use solution, and includes a preservative.

6. The system of claim 3 wherein said douche formulation preservative includes naturally-occurring sorbic acid.

7. The system of claim 3 wherein said external vulval wipe solution non-ionic surfactant includes sorbitan sterate.

8. The system of claim 3 wherein said external vulval wipe solution non-ionic surfactant includes polyoxyethylene fatty acid esters.

9. The system of claim 3 wherein said external vulval wipe solution anti-inflammatory agent includes hydrocortisone acetate.

10. The system of claim 3 wherein said external vulval wipe solution preservative is a mixture of methyl paraben, propyl paraben, imidazolinyl urea and propylene glycol.

11. A process for cleansing the vaginal area comprising the steps of introducing into the vaginal cavity an internal vaginal douche formulation which comprises (1) a solution of inorganic salts that mimic the electrolyte balance of normal tissue selected from the group comprising sodium acetate, sodium chloride, magnesium chloride, potassium chloride and sodium glucontae; (2) a buffering agent, and optionally; (3) a preservative, and wherein said external vulval wipe product is a towelette impregnated with a solution which comprises (a) caprylic/capric triglyceride; (b) at least one non-ionic surfactant; (c) an anti-inflammatory agent; and (d) citric acid.

12. The process of claim 11 wherein said balanced electrolyte solution comprises an aqueous solution of sodium chloride, potassium chloride, magnesium chloride hexahydrate, sodium acetate, and sodium gluconate.

13. The process of claim 11 wherein said douche formulation is in the form of a ready-to-use solution.

14. The process of claim 11 wherein said douche formulation preservative includes naturally-occurring sorbic acid.

15. The process of claim 11 wherein said external vulval wipe solution non-ionic surfactant includes sorbitan stearate.

16. The process of claim 11 wherein said external vulval wipe solution non-ionic surfactant includes polyoxyethylene fatty acid esters.

17. The process of claim 11 wherein said external vulval wipe solution anti-inflammatory agent includes hydrocortisone acetate.

18. The process of claim 11 wherein said external vulval wipe solution includes a preservative.

19. The process of claim 11 wherein said external vulval wipe solution preservative is a mixture of methyl paraben, propyl paraben, imidazolidinyl urea and propylene glycol.

20. An internal vaginal douche formulation comprising a solution containing balanced electrolytes wherein said balanced electrolyte solution comprises an aqueous solution of sodium chloride, potassium chloride, magnesium chloride hexahydrate, sodium acetate, and sodium gluconate.

21. The formulation of claim 20 wherein said douche formulation is in the form of a ready-to-use solution, and includes a preservative.

22. The formulation of claim 21 wherein said douche formulation preservative includes naturally occurring sorbic acid.

23. The formulation of claim 20 comprising: about 0.516% to about 0.536% by weight potassium chloride; about 0.02% to about 0.035% by weight magnesium chloride hexahydrate; about 0.212% to about 0.232% by weight sodium aceate, and about 0.492% to about 0.512% by weight sodium gluconate.

24. The formulation of claim 20 further comprising a buffering agent.

25. The formulation of claim 24 wherein said buffering agent comprises about 0.25% to about 0.50% by weight citric acid.

26. The formulation of claim 22 wherein said preservative comprises about 0.09% to about 0.11% by weight naturally occurring sorbic acid.

27. An external vulval wipe solution comprising (a) caprylic/capric triglyceride; (b) at least one non-ionic surfactant; (c) an anti-inflammatory agent; and (d) citric acid.

28. The formulation of claim 27 wherein said external vulval wipe solution non-ionic surfactant includes sorbitan sterate.

29. The formulation of claim 27 where said external vulval wipe solution non-ionic surfactant includes polyoxyethylene fatty acid esters.

30. The formulation of claim 27 wherein said external vulval wipe solution anti-inflammatory agent includes hydrocortisone acetate.

31. The formulation of claim 27 wherein said external vulval wipe solution includes a preservative.

32. The formulation of claim 27 wherein said external vulval wipe solution preservative is a mixture of methyl paraben, propyl paraben, imidazolidinyl urea and propylene glycol.

33. The formulation of claim 27 in combination with a towlette impregnated with said formulation.

34. The formulation of claim 27 comprising about 5% to about 20% by weight caprylic/capric triglyceride.

35. The formulation of claim 27 comprising about 2% to about 4% by weight sorbitan stearate.

36. The formulation of claim 27 comprising about 1% to about 3% by weight of a nonionic surfactant obtained by esterification of sorbitol with a fatty acid.

* * * * *

UNITED STATES PATENT AND TRADEMARK OFFICE
CERTIFICATE OF CORRECTION

PATENT NO. : 4,788,060

DATED : November 29, 1988

INVENTOR(S) : Clarence J. Endicott and Donald E. Hartung

It is certified that error appears in the above-identified patent and that said Letters Patent is hereby corrected as shown below:

Column 2, line 43.
Should be typed as: "ries), is a product used intravenously in hospitals as an"

Column 3, Line 9.
Should be typed as: "tion of seawater, contain detergents. The more com-"

Signed and Sealed this

Thirteenth Day of February, 1990

Attest:

JEFFREY M. SAMUELS

*Attesting Officer*      *Acting Commissioner of Patents and Trademarks*